United States Patent [19]
Laurie et al.

[11] Patent Number: 5,895,812
[45] Date of Patent: *Apr. 20, 1999

[54] DIAGNOSTIC FOR SJOGREN'S SYNDROME

[75] Inventors: Gordon W. Laurie; Rebecca A. Ogle; J. Douglas Glass, all of Charlottesville, Va.

[73] Assignee: The University of Virginia Alumni Patent Foundation, Charlottesville, Va.

[*] Notice: This patent issued on a continued prosecution application filed under 37 CFR 1.53(d), and is subject to the twenty year patent term provisions of 35 U.S.C. 154(a)(2).

[21] Appl. No.: 08/432,055

[22] Filed: May 1, 1995

[51] Int. Cl.⁶ .................................................. C07K 16/18
[52] U.S. Cl. ............................ 530/388.2; 530/388.24; 530/868
[58] Field of Search ........................ 530/388.2, 388.24, 530/389.2, 868

[56] References Cited

PUBLICATIONS

H.J. Ellis et al, GUT, 33, 1504–1507, 1992.
G.W. Laurie et al, Invest. Opthamol. & Visual Science, 35, 1825, 1994.
G.W. Laurie et al, Biochem. Biophys. Research Communic. 217, 10–15, 1995.
E. Harlow et al, Antibodies: A Laboratory Manual, Cold Spring Harbor Laboratory, 1988, pp. 61–71.
J.W. Goding, Monoclonal Antibodies: Principles and Practice, Academic Press, 1986, pp. 282–286.
E. Harlow et al, Antibodies: A Laboratory Manual, Cold Spring Harbor Laboratory, 1988, pp. 23–28.

*Primary Examiner*—David Saunders
*Attorney, Agent, or Firm*—Oblon, Spivak, McClelland, Maier & Neustadt, P. C.

[57] ABSTRACT

The present invention relates to a novel polypeptide which has secretion enhancing activity on lacrimal and parotid gland cells, monoclonal antibodies thereto, and methods of diagnosising Sjorgren's syndrome using these antibodies.

1 Claim, 11 Drawing Sheets

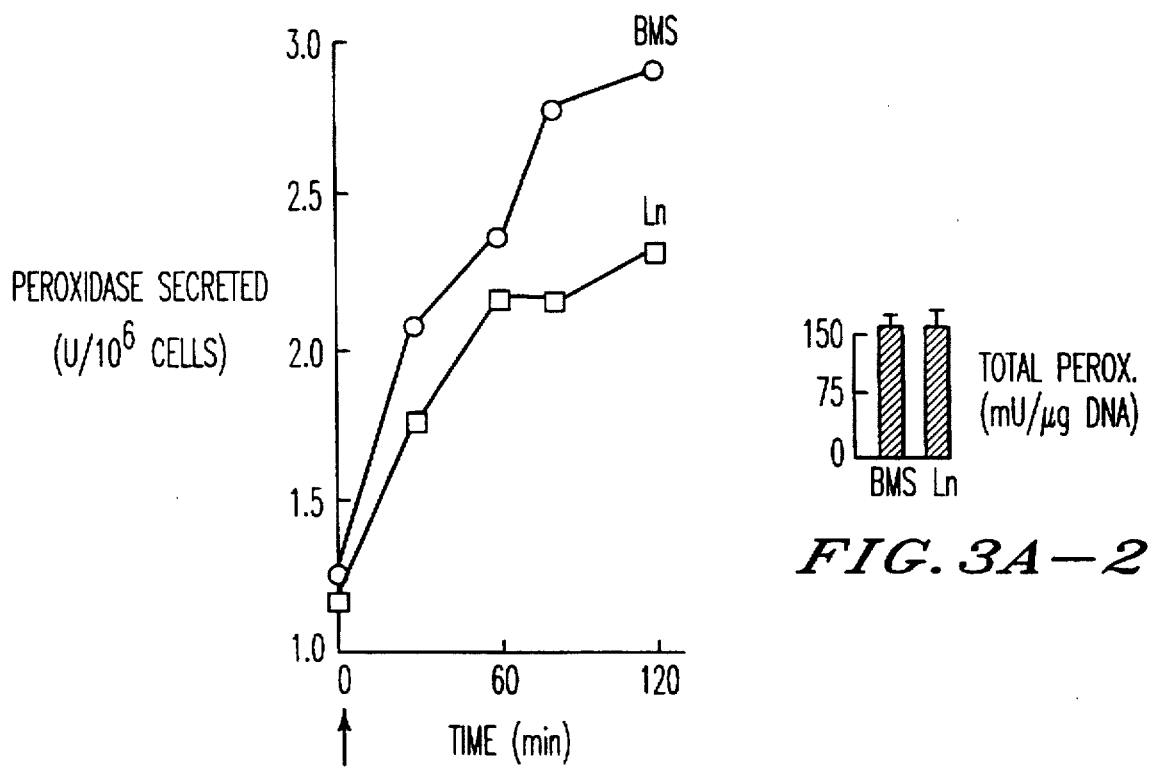
FIG. 3A-1
FIG. 3A-2
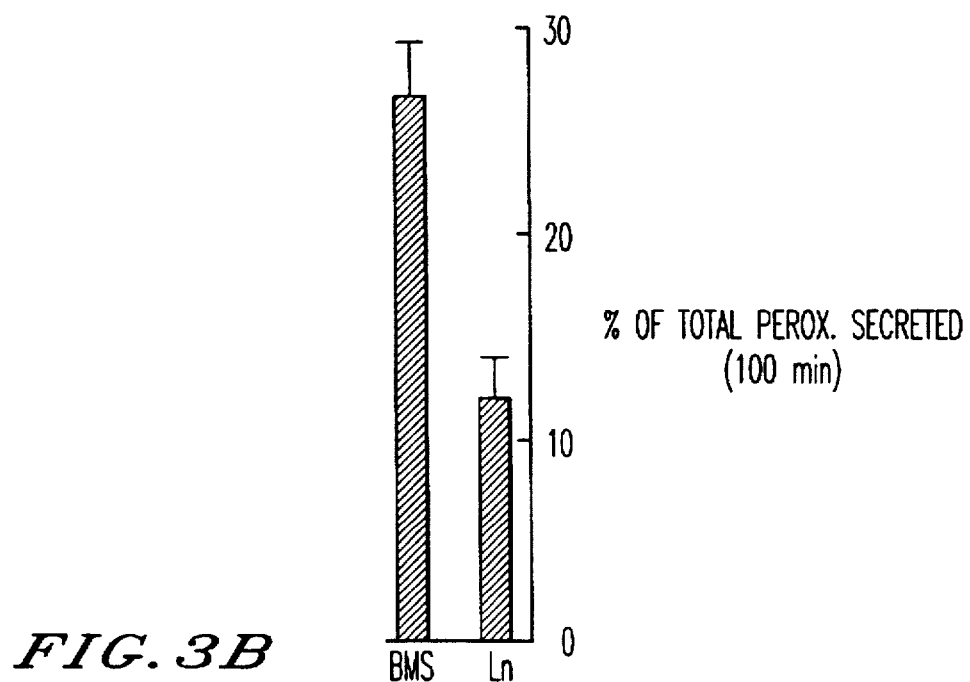
FIG. 3B

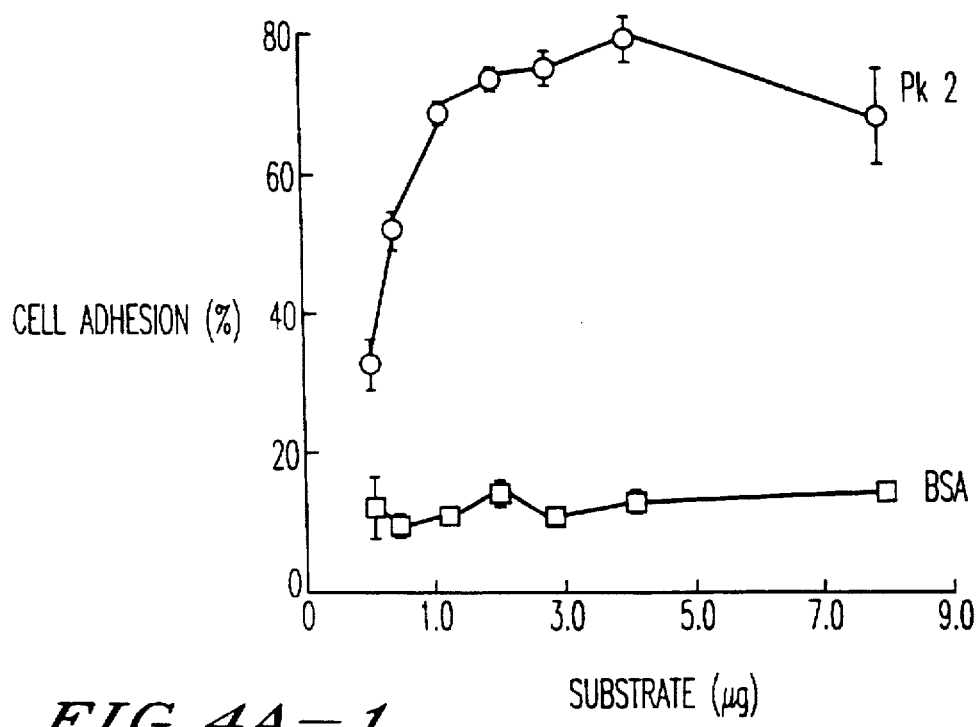
*FIG. 4A-1*
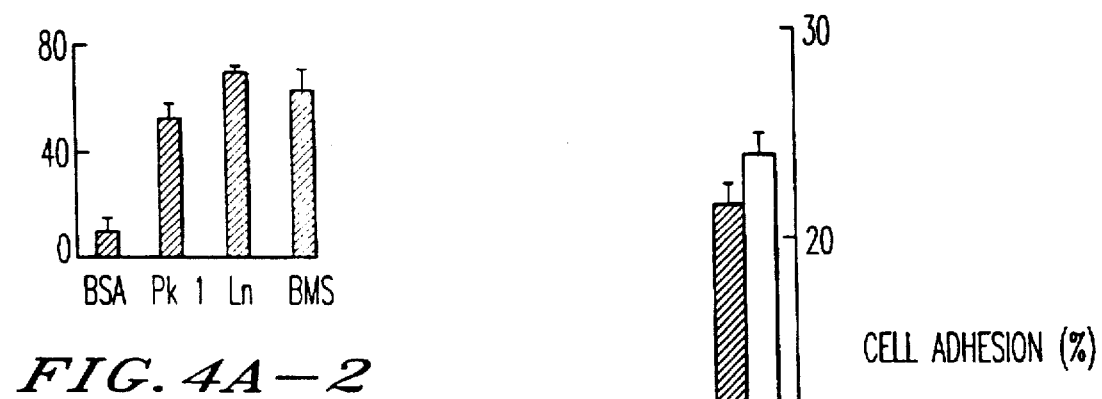
*FIG. 4A-2*
*FIG. 4B*
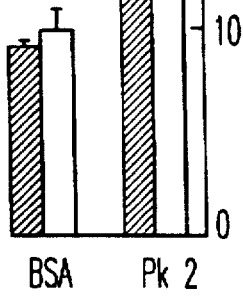

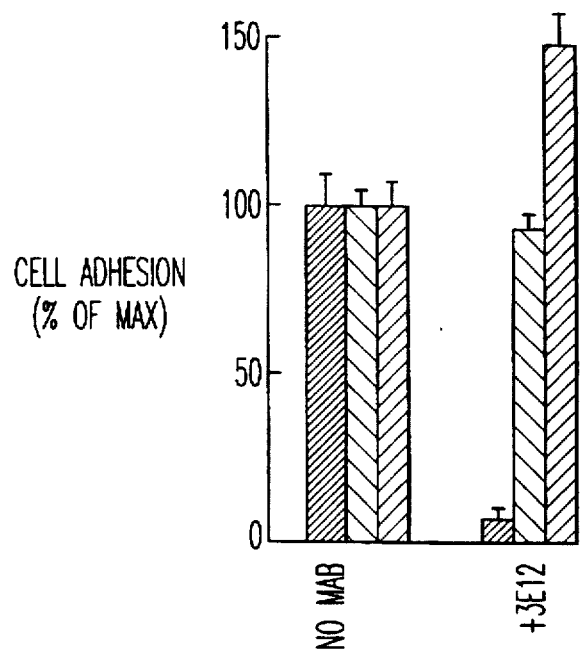
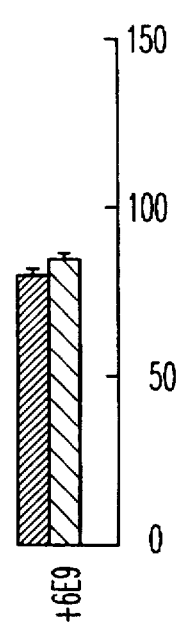
FIG. 6A  FIG. 6B
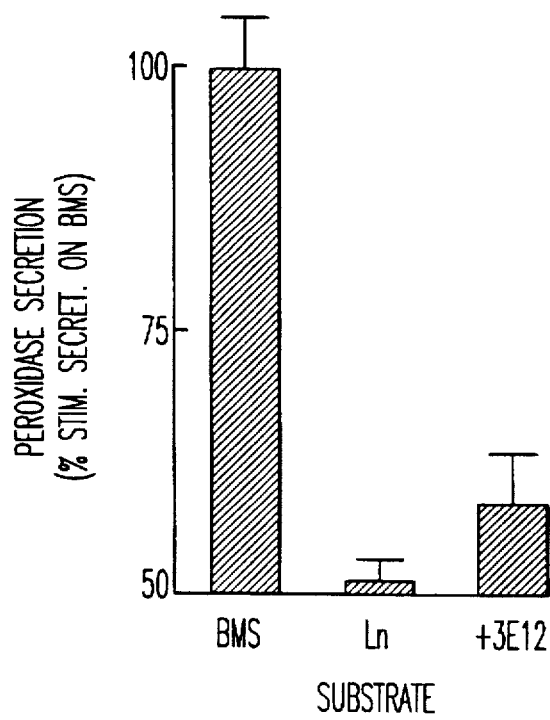
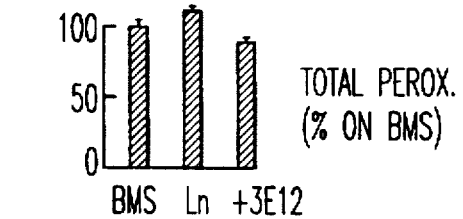
FIG. 6C-2
FIG. 6C-1

DIAGNOSTIC FOR SJOGREN'S SYNDROME

The invention was in part funded by a National Institutes of Health grant. The government may have certain rights in this application.

BACKGROUND OF THE INVENTION

1. Field of the Invention

The present invention relates to a novel polypeptide which has secretion enhancing activity on lacrimal and parotid gland cells, monoclonal antibodies thereto, and methods of diagnosing Sjogren's syndrome using these antibodies.

2. Discussion of the Background

Sjogren's syndrome is the second most common autoimmune disease and is a triad of disease including rheumatoid arthritis and dry eye.

Dry eye, the ocular component of Sjogren's syndrome, is a condition of the eye and or the adnexa that usually causes a feeling of discomfort such as ocular dryness, grittiness, burning, soreness or scratching, to the patient. Many theories have been offered to explain the possible causes of dry eye. These theories range from the simple to the complex and include inadequate Meibomian gland secretion, insufficient tear volume, mucous deficiency, evaporative losses from the tear film and failure to form an adequate tear film. Proposed causes for dry eye, treatment and symptoms are described in a compendium of papers on the subject edited by Holly, The Preocular Tear Film In Health, Disease, and Contact Lens Wear, The Dry Eye Institute, Lubock, Tex., 1986, incorporated herein by reference.

Despite these theories, the cause of dry eye has yet to be definitely determined. Currently, dry eye is treated with ophthamalic solutions which represent "artificial tears". Such compositions are methods of treatment are described in U.S. Pat. No. 4,914,088. There remains a need for understanding the cause of dry eye such that better treatments can be developed.

Despite the large population affected by Sjogren's syndrome, to date no accurate diagnostic assay is available. Rose Bengal staining of nasal conjunctiva cornea and temporal conjuctivaassessed with a semiquantitative scoring system is described in Ann. Ophthalmol. 5:859, 1973. The tear film breakup time test assesses stability of tear film as described in Arch. Ophthalmol. 89:103, 1973. Schirmer test assesses the ability of the lacrimal gland to produce reflex tears as described in Am. J. Ophthalmol. 66:70, 1968. The tear film osmolarity test is described in Arch. Ophthalmol. 96:677, 1978. None of these tests are especially sensitive or specific. Accordingly, there is a also need for accurate diagnostic means.

SUMMARY OF THE INVENTION

Accordingly, one object of this invention is to provide a novel polypeptide which has tear secretion enhancing activity on lacrimal and parotid gland cells.

A second object of the present invention is to provide novel antibodies, particularly monoclonal antibodies, to these polypeptides.

A third object of the present invention is to provide methods for diagnosing Sjogren's syndrome using these antibodies.

A fourth object of the present invention is to provide kits for assaying for Sjogren's syndrome.

These and other objects that will become apparent hereinafter have now been achieved by the present inventor's discovery of a novel basement membrane protein enriched in lacrimal and parotid exocrine secretory glands (hereinafter BM180).

BRIEF DESCRIPTION OF THE DRAWINGS

FIG. 1a: The large laminin/entactin complex ('Ln/En'; peak 1) runs just after the void volume ($V_o$). Uncharacterized peak 2 (horizontal bar) from several runs was pooled, concentrated and rerun; profile is seen inset, $V_t$, total column volume. FIG. 1b: Electrophoretic analysis of BMS and peak 2. Lane 1: BMS; lanes 2–4: increasing amounts of peak 2 (Pk 2). Samples were analyzed on a 5–15% polyacrylamide gradient SDS gel in the absence (−) of dithiothreitol (DTT). Arrowhead points to approximate location of BM180. Shown at left are positions of molecular weight markers run in the presence of DTT.

FIG. 2a: Addition of carbachol and vasoactive intestinal peptide (VIP) (arrow) stimulates exocytosis of stored secretary granule peroxidase ('stim'); in the absence of stimulation, peroxidase secretion is via the constitutive pathway ('unstim'). Values are normalized to cellular DNA. Level of carbachol and VIP used in this and all subsequent figures is $10^{-4}$ M and $10^{-8}$ M, respectively. Inset, lacrimal acinar cells attached to BMS 24 hr after plating as viewed by Hoffman optics. Characteristic secretary granules are apparent. FIG. 2b: Parallel examination of cell viability (MTT assay) in the presence or absence of carbachol and VIP. Values in FIGS. 2a and 2b are from a representative experiment performed in triplicate using gelled BMS.

FIGS. 3a and 3b. Removal of peak 2 from BMS decreases the capacity for regulated peroxidase secretion by approximately 50% without affecting total cellular peroxidase. FIG. 3a: Representative time course experiment comparing regulated secretion by cells adherent to gelled BMS vs to equal milligram amounts of purified gelled laminin (Ln). Arrow indicates addition of carbachol and VIP. Inset, Total peroxidase in BMS and laminin adherent cells does not differ, suggesting that peroxidase enzyme biosynthesis is similar. Values are from two (Ln) to four (BMS) independent experiments each performed in duplicate or triplicate. FIG. 3b: Cumulative regulated secretion for the first 100 min of stimulation expressed as per cent of total peroxidase from five (Ln) to six (BMS) independent experiments each performed in triplicate. Cumulative release on laminin is therefore half that of BMS.

FIGS. 4a and 4b. Peak 2 contains cell adhesion activity. FIG. 4a: Dose dependent attachment of HT1080 cells to peak 2 (Pk 2) but not bovine serum albumin (BSA). Substrate values indicate coating solution per well; lowest concentration was 0.04 μg/well. Inset, HT1080 cells adhere at similar levels to peak 1 (Pk 1), laminin (Ln) and BMS. Coating solution was 4 μg/well. FIG. 4b: Attachment of freshly isolated lacrimal acinar cells to peak 2 vs BSA. Coating solution was 4 (dark bar) and 8 (white bar) μg/well. Values are expressed as per cent adhesion to poly D lysine.

FIGS. 5a–5d: Micrographs of a representative adhesion blot illustrating areas without (FIG. 5a; only one cell present) or with (FIGS. 5b–5d) adherent cells which appear as dark dots (from amido black staining; protein bands are not visible because of a BSA blocking step). Electrophoretic migration in original gel was from left to right; micrographs represent (top to bottom) full width of a gel lane. Bar=0.004 Rf. FIG. 5e: Quantitation of number of attached cells (solid line) per Rf value in the same adhesion blot with location of regions (a)–(d) indicated. Approximate size of adhesion activity was determined from standard curve (dashed line). Inset, blot not used for cell adhesion stained directly with amido black to reveal peak 2 proteins; arrowheads indicate bands with same size as adhesion activity. Quantitation was performed by determination of cell number throughout the width of a single lane on the blot at 0.018 Rf intervals.

FIGS. 6a–6c. Anti-peak 2 monoclonal antibody (mab) 3E12 inhibits both peak 2 cell adhesion and secretion enhancement activity. FIG. 6a: 3E12 mab inhibits adhesion only to peak 2 (solid) and not to laminin (wide slash) or collagen IV (narrow slash). FIG. 6b: 6E9, one of several anti-peak 2 mab's which did not inhibit cell adhesion to peak 2. Representative experiment carried out in triplicate. FIG. 6c: Preincubation of BMS with 3E12 mab inhibits peak 2 secretion enhancing activity. Cells were stimulated for 100 min. Values are normalized to cell number and are from three independent experiments performed in triplicate or duplicate; t test comparing BMS vs BMS+3E12 revealed a p value less than 0.001. Inset, total peroxidase in adherent cells is unaffected by 3E12 mab; t test comparing BMS vs BMS+3E12 indicated no significant difference (p<0.5).

FIG. 7a: Constitutive secretion (unstim) by lacrimal acinar cells adherent for 24 hr to laminin (Ln) alone or laminin plus increasing amounts of peak 2 (pk 2) remains constant. FIG. 7b: Regulated secretion by the same 24 hr cultures increases in a peak 2 dose dependent fashion. Cells were stimulated for 100 min. Amount of laminin (Ln) used throughout was 4 µg/well. t test of regulated secretion on wells treated with 4 µg laminin/8 µg peak 2 vs 4 µg laminin/0.04 µg peak 2 reveals a p value of 0.03. Regulated secretion on wells coated with 10 µg of peak 2 or laminin alone was 54 and 59% of maximum, respectively. Inset, 3E12 mab preincubated with coated laminin and peak 2 (4 µg each) inhibits regulated secretion in a dose dependent manner. Control (ctrl) rat IgG has no effect t test of 3E12 vs control IgG (10 µg) p value is 0.026. Representative experiment carried out in triplicate.

DESCRIPTION OF THE PREFERRED EMBODIMENTS

Polypeptides

Figures 1, 1A:
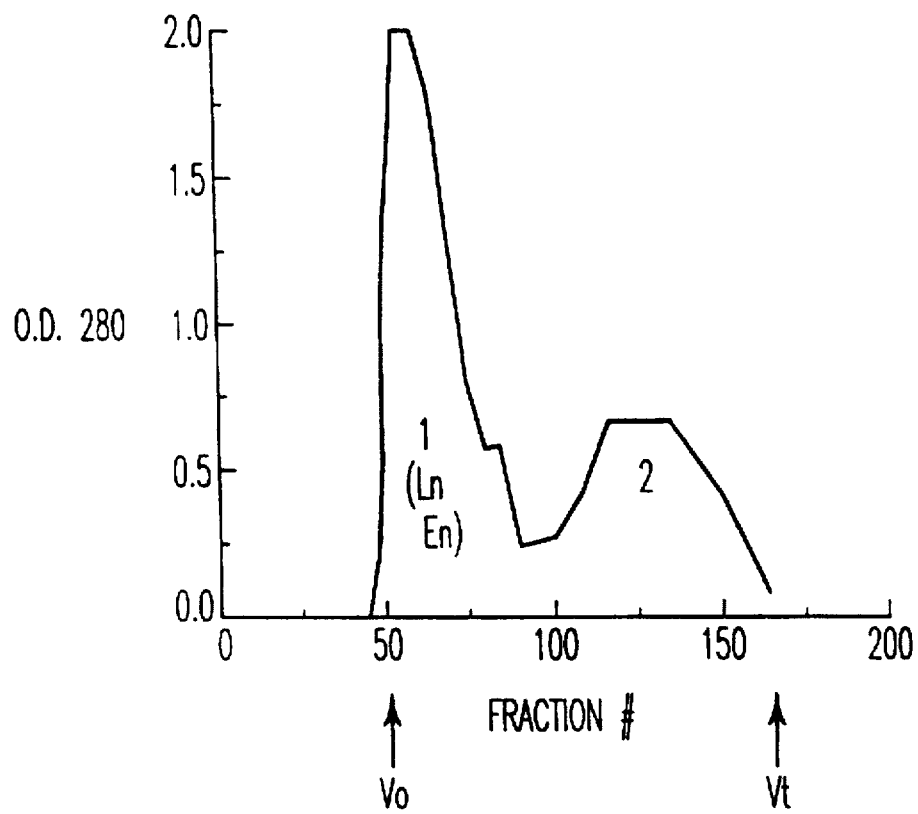
FIGS. 1a and 1b. Separation of basement membrane substrate (BMS) into two peaks by gel filtration.

BM180 is a protein found in the basement membrane substrate (BMS) which is known to support both adhesion and secretogogue responsiveness in primary cultures of rat lacrimal acinar cells. BM180 has cell adhesion activity and can be isolated from basement membrane using monoclonal antibodies prepared against a lower molecular weight peak isolated from basement membrane substrate by gel filtration.

Moreover, BM180 has secretion enhancing activity, in particular tear secretion activity and likely salivary secretion activity. Secretion enhancing activity means that the protein is capable of increasing the amount of secreted material produced by an animal by at least 30%, preferably 50%, compared to the animal's normal secretion in the absence of BM180.

BM180 has a mobility of 180 Kda and 60 Kda in the absence or presence of dithiothreitol (DTT), respectively; and shows no apparent immunological identity by competitive enzyme-linked absorbent assay (ELISA) with laminin, collagen IV, entactin, fibronectin, BM-40, perlecan or vitronectin.

BM180 can be purified from peak 2 by immunopurification on a 3E12 mab column.

Antibodies

Novel antibodies which bind to BM180 can be prepared using conventional techniques, such as that provided by Cooksley et al, MATRIX 10:285–291, 1990. Suitable antibodies are any monoclonal antibodies which specifically bind BM180. Typically, such antibodies will bind to BM180 with a $K_D$ of greater than $10^6$ mol$^{-1}$, preferably greater than $10^7$ mole$^{-1}$, more preferably greater than $10^8$ mol$^{-1}$.

Suitably, a mouse is injected with BM180 or laminin-immunodepleted BMS. To enhance the immune response and production of antibodies, BM180 or laminin-immunodepleted BMS can be administered to the mouse in admixture with an adjuvant, such as Freund's Complete Adjuvant.

Typically, BM180 or laminin-immunodepleted BMS is administered by injecting them interperitoneally into a rat, mouse, rabbit or other suitable host (see Enriquez et al, Hybridoma, vol. 10, p. 745 (1991)). The host is then sacrificed, and the spleen is aseptically removed. Spleen cells are then hybridized with myeloma cells, and the resulting hybrids screened for the production of monoclonal antibodies which bind specifically to BM180. Such screening may be carried out by means of ELISA and Western blotting.

One monoclonal antibody in accordance with the present invention (referred to hereinafter as 3E12) is expressed by a hybridomal cell line which was deposited with the American Type Culture Collection (ATCC), Rockville Md. under accession number HB-11879 on Apr. 27, 1995.

Preincubation of basement membrane with 3E12 decreased regulated peroxidase secretion by one-half without affecting constitutive secretion nor the amount of cellular peroxidase available for release. Adding back Pk 2 restored regulated secretion in a dose dependent and 3E12 inhibitable manner; suggesting a synergistic relationship between BM180 and laminin.

In a preferred embodiment, the monoclonal antibody is labelled. The label may suitably be any which is conventionally attached to monoclonal antibodies for use in an immunoassay, such as an enzyme (e.g., horseradish peroxidase), a chromophore, a fluorophore, or a radiolabel. The label may be bonded to the monoclonal antibody by any conventional method including via conventional crosslinking agents. For Western blots, it is preferable to use goat anti-rat IgG conjugated to horseradish peroxidase (TAGO, Inc., Burlingame, Calif.) to bind the monoclonal antibody and to use ImmunoSelect 4-chloro-1-napthol (4CN, Gibco BRL, Life Technologies, Inc., Gaithersburg, Md.) for detection. A more sensitive detection system for Western Blots is also used with using enhanced chemiluminescence (ECL, Amersham, Northbrook, Ill.) exposed on X-ray film (Eastman Kodak, Rochester, N.Y.). Biotinylated goat-anti-rat immunoglobulins with Extravidin (an alkaline phosphatase conjugate available from Sigma Chemical Company, St. Louis Mo.) can also be used for detection of Western blots. For immunofluorescence photography, biotinylated sheep anti-rat Ig and streptavidin Texas red or streptavidin fluorescein for detection (Amersham International, Amersham UK) can be used.

Methods of Diagnosis

In another embodiment, the present invention provides methods of detecting the presence of Sjogren's syndrome by screening for the depletion or absence of BM180 in lacrimal or parotid gland tissue. "Depletion" as used herein means that the amount of BM180 in either lacrimal or parotid gland tissue is reduced in comparison to a normal, healthy adult free from Sjogren's syndrome. Typically, depletion entails the reduction of the amount of BM180 in these tissues by greater than 20%, preferably by greater than 30%, more preferably by greater than 40%.

Preferred immunologic means of detecting BM180 in these tissues are the ELISA method and Western blotting methods. These techniques are well described in the art.

A preferred immunologic means of detecting BM180 is the ELISA method. ELISA plates can be purchased commercially purchased (for example, from Falcon, Fischer Scientific, Pittsburgh, Pa.). A sample of lacrimal and parotid tissue can than contacted with these plates. The samples are preferably prepared by extracting BM180 from the tissues and resuspending the BM180 extract in an incubation-suitable buffer to about a 10 g/mL concentration. One such solution contains 50 Mm sodium phosphate, 0.1 M sodium chloride, 0.02% Tween 20 and 0.1% bovine serum albumin (BSA). Another such solution contains 0.16% sodium carbonate, 0.29% sodium bicarbonate, pH 9.6

The samples are placed in the well, incubated at a temperature ranging from about 4° C. to about 37° C., and preferably at about 37° C. for a time period of from about 1 hour to overnight and preferably about one hour. The wells containing the sample are washed thoroughly before introducing a detection antibody into the well such as the labeled antiBM180 antibodies described above. The antibodies are preferably added after being diluted in an incubation buffer to a concentration of about 1/50 or 0.5 µg/mL.

The wells are incubated for about 1 hour and thereafter washed thoroughly and prepared using standard ELISA techniques known to the art, such as including the amplifying goat antibodies to rat IgG conjugated with horseradish peroxidase. The wells are then washed and 100 microliters of substrate buffer (such as ABTS) is added to generate a color reaction which can be quantitated using any suitable reading device such as the ELISA reader available from Dynatech 700, Chantilly Va.

Alternatively, Western blots can be used to determine the amount of BM180 in a sample. For Western blots a typical procedure includes suspending BM180 extract in a sample buffer and boiling for 5 min prior to being applied to 8–12% PAGE and transferred to Western blots.

Alternatively, immunoprecipitation can be used to determine the amount of BM180 in a sample. For immunoprecipitation a typical procedure includes: monoclonal antibody is conjugated to HZ Beads (Sigma Chemical Co., St. Louis, Mo.). Antibody beads are added to the BM180 extract and protein is allowed to bind (~10 min). The beads are then washed three times, boiled in sample buffer and the sample buffer is applied to 8–12% PAGE. The presence of protein can be determined directly by Commassie blue staining of the gels or by Western blot.

Alternatively, any other method for selectively detecting the presence of BM180 by measuring the amount of BM180, if any, which binds to the present monoclonal antibody can be used including any conventional immunoassay which relies upon the binding of BM180 to anti-BM180 antibody. Thus, the present assay may be a sandwich assay, a displacement assay, a competitive assay, etc. Such assays are described in "Guide to Protein Purification", *Methods in Enzymology*, vol. 182, edited by M. P. Deutscer, Academic Press, Inc., Harcourt, Brace, Jovanovich, Publishers: San Diego, Calif., 1990 and in "Antibodies: A Laboratory Manual", by E. Harlow, Cold Spring Harbor Laboratoy and D. Lane, Imperial Cancer Research Fund Laboratories, 1988; which are incorporated herein by reference.

Using the methods of the present invention, it is possible to detect BM180 in a sample containing as little as about 10 ng.

The presence of non-human BM180 corresponding to the BM180 of the present invention can also be detected using the monoclonal antibodies of the present invention as they likely cross-react with BM180 from other species (including mammals, preferably, dogs, cats, sheep, horses, porcine and bovine).

Having generally described this invention, a further understanding can be obtained by reference to certain specific examples which are provided herein for purposes of illustration only and are not intended to be limiting unless otherwise specified.

EXAMPLES

Preparation of Substrates—A 10 Mm EDTA extract of Engelbreth-Holm-Swarm (EHS) tumor matrix was prepared at 4° C. essentially according to the method of Paulsson et al (29) with slight modifications (28). For gel filtration (4° C.), BMS was passed over a Biogel A 1.5 m column (2.5×100 cm; refs 28, 29) resulting in separation of the laminin-entactin complex from a broad peak of uncharacterized basement membrane material (hereafter referred to as 'peak 2'). Occasional contaminating 400 kD and 200 Kd laminin bands were removed by repassage over the Biogel A1.5 m column, or by overnight (4° C.) incubation with an antilaminin antibody-Sepharose column. Protein concentration was determined by the Lowry assay as modified by Markwell et al (30).

Purified laminin was prepared (generously supplied by Dr. Roy Ogle, University of Virginia, Charlottesville Va.) according to a modification (Ogle, unpublished) of the Kleinman et al (31) method. Also used was collagen IV (from Dr. Roy Ogle; University of Virginia, Charlottesville Va.), BM-40 (from Dr. Larry Fisher; National Institute of Dental Research, Bethesda Ms.), perlecan core protein (from Dr. John Hassell; Eye and Ear Institute, Pittsburgh Pa.; 32) and recombinant entactin (from Dr. Jay Fox; University of Virginia, Charlottesville Va. and from Dr. Albert Chung; University of Pittsburgh, Pittsburgh Pa.). Vitronectin was purchased from Telios (San Diego Calif.) and fibronectin from Sigma (St. Louis Mo.).

Figures 1, 1A, 2:
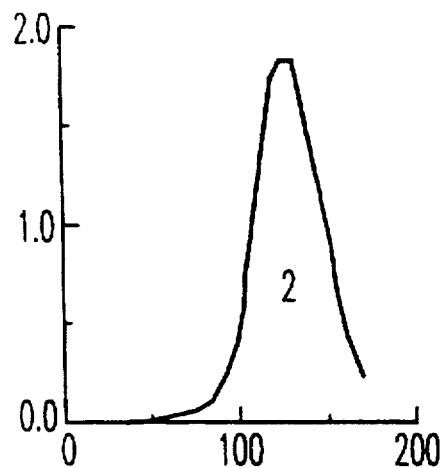
Figure 7A:
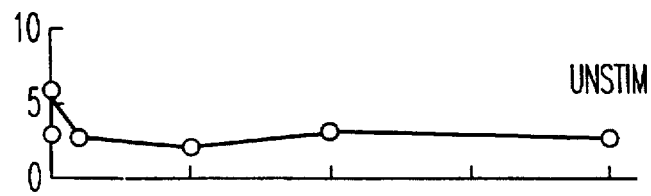
FIGS. 7a and 7b. Addback of peak 2 to laminin promotes a dose dependent increase in regulated secretion which is inhibited with 3E12 mab.

Isolation of Lacrimal Acinar Cells—Rat lacrimal acinar cells were isolated from male 4–6 wk Sprague-Dawley rats (Hilltop, Scottdale Pa. or NCI, Frederick Md.) using the methods of Oliver et al (24) and Hann et al (33) with the addition of an initial Dulbecco's modified Eagle's medium (DMEM) intracardiac perfusion to wash out the vasculature and a later centrifugation step on a 10/30/60% discontinuous Percoll (rather than Ficoll) gradient for 15 min at 50 g with collection of lacrimal acinar cells at the 30/60% interface. Cell purity was 98% as assessed using Hoffman modulation contrast optics by which secretary granules were clearly visible. Viability, determined by trypan blue exclusion, was 85–95%. Cells were plated at $1.9 \times 10^5$ cells/cm$^2$ in 48 or 96 well plates on a preformed gel (0.63 mg/cm$^2$) of BMS or purified laminin. In addback experiments, cells were plated on coated substrates (coating solution 14.3–42.9 µg/cm$^2$; described shortly). Similar levels of secretion were obtained on gelled and coated substrates (compare FIGS. 2 and 7). Plating medium was high glucose DMEM containing dexamethasone (1 µg/ml), putrescine (1 mM) epidermal growth factor (EGF) (50 µg/ml), L-ascorbic acid (25 µg/ml), insulin (6 µg/ml), transferrin (6 µg/ml), selenous acid (6 µg/ml), reduced glutathione (10 µg/ml), Hepes (15 mM), heat inactivated fetal calf serum (10%) and gentamicin (50 µg/ml). Gelled BMS or laminin substrates for cell culture were prepared prior to plating by addition of 132 (48 well) or 40 (96 well) µl/well of BMS or laminin (diluted to 4.5 mg/ml in DMEM; 4° C.) to plates kept chilled on ice, followed by incubation for 1 hr at 37° C. Temperature dependent polymerization of laminin (34)—together in BMS with collagen IV, perlecan (35) and likely other components—leads to the efficient formation of a gel for which the protein concentration of the starting material may be presumed to approximate that of the gel itself (36). Concentration of gelling substrate together with the calculated bottom surface area of a well was expressed as mg/cm$^2$. In antibody experiments, gelled BMS was incubated with experimental antibody (as hybridoma supernatant initially at 100 µl/well in 48 well plates, and later purified from ammonium sulfate concentrated supernatant on a goat anti-rat IgG, F(ab')$_2$ [Jackson Immunoresearch; West Grove Pa.] specific column; 50 µg/well, 96 well plate) for 1 hr at 37° C. and washed two times with medium prior to addition of cells.

In peak 2 addback experiments, cells were plated on coated rather than gelled substrates since peak 2 gelled poorly with purified laminin. Coating was carried out overnight at 4° C. in 96 well plates using a constant amount of laminin (2 or 4 µg/well) and increasing amounts of peak 2 (0–8 µg/well), both of which were diluted in water. In control experiments, wells were coated with increasing amounts of peak- 2, laminin or BMS alone. For antibody inhibition studies, wells incubated with a coating solution of 4 µg/well each of peak 2 and laminin were blocked with 1% BSA (Sigma, St. Louis Mo.) for 4 hrs (4° C.), incubated with purified experimental antibody or rat control IgG (Sigma, St. Louis Mo.) at increasing concentrations (0, 2, 10 µg/well) overnight at 4° C., washed twice with DMEM, and then plated with cells.

Secretion Studies—Secretion studies were performed on cells plated for 24 hr on BMS (with or without antibody), laminin, peak 2 and laminin plus peak 2 (with or without antibody). Adhesion was approximately 92% of plated cells, irrespective of gelled or coated substrate, or presence of antibody. This level exceeds that observed in cell attachment studies, because of the presence of serum and the duration of plating. Cellular viability after stimulation was examined using the MTT (3-[4,5-dimethylthiazol-2-yl]-2,5-diphenyl tetrazolium bromide) assay (Chemicon, Temecula Calif.). To evaluate secretion, 24 hr culture media was removed, cultures were washed twice and fresh medium was added which at 15 min intervals (separate wells in triplicate), or after 100 min, was collected and gently spun to remove any floating cells. For stimulation, fresh medium containing $10^{-4}$ M carbachol and $10^{-8}$ M VIP (26) was added, and aliquots were removed in a similar fashion at 15 min intervals, or only once 100 min after stimulation. The cell layer was detached with dispase (40 U/ml; Collaborative Research, Bedford Mass.) and trypsin-EDTA (0.1%/1.1 mM, respectively; Gibco BRL, Grand Island N.Y.) for 30 min at 37° C. with agitation. Detached cells were combined with centrifuged cell pellets from media samples, resuspended in media and stored at −80° C. Cell pellet samples were sonicated prior to enzyme assay. Quantity of the secretary protein peroxidase was enzymatically determined using the lacrimal gland peroxidase method of Herzog et al (21), as volume adapted to a 96 well plate format. The room temperature V$_{max}$ of each reaction was simultaneously determined using a kinetic plate reader (450 nm filter; Molecular Devices, Menlo Park Calif.) online with a Macintosh LC computer. Results were expressed as milliunits (mu; using E=3.16 mM$^{-1}$cm$^{-1}$) according to Herzog et al (21). Total cellular peroxidase was defined as the sum of peroxidase detected in cell pellet, unstimulated media and stimulated media samples combined. DNA content in cell pellet aliquots was determined (37) with a fluorometer (Hoefer Scientific Instruments, San Francisco Calif.) adapted for use with capillary tubes. No contaminating DNA could be detected in wells containing BMS alone, which after dissolution with dispase and trypsin did not contribute to the cell pellet.

Cell Attachment Studies—Attachment to peak 2 by freshly isolated lacrimal acinar or HT1080 human fibrosarcoma cells (ATCC, Rockville Md.) was examined by the crystal violet detection method of Aumailley et al (38). Wells of 96 well plates were coated (100 µg/well) overnight at 4° C. in triplicate or quadruplicate with 0.04–8 µg/well of peak 2, peak 1, laminin, BMS or BSA (Sigma, St. Louis Mo.), or 100 µg/well of poly D lysine (Sigma, St. Louis Mo.) in water. Wells were blocked with 1% BSA and plated with $2 \times 10^4$ cells per well in medium without serum, and adhesion evaluated (38). Substrate coating efficiency is presumed to be 7–10% based on Aumailley et al (39) using laminin under identical coating conditions. Blot attachment assays (40) were carried out after separating DTT reduced peak 2 on 7–20% or 5–15% SDS PAGE gels and transfer to Immobilon (Millipore; Bedford Mass.) using a 1% BSA block and $1.6 \times 10^6$/ml HT1080 cells incubated with blots for 60 min (37° C.) in serum-free medium.

Preparation of Monoclonal Antibodies—Six LOU/M rats (149 g;NCI, Frederick Md.) were immunized with laminin-immunodepleted peak 2 (200 µg/rat) in complete Freund's adjuvant and boosted 3 wks later (200 µg/rat) in incomplete Freund's adjuvant. One boost was carried out 3 months later with a final intravenous boost three days prior to fusion. Immune and control preimmune tail bleeds were assessed by ELISA (41) and Western blotting (42) for reactivity with peak 2 using a secondary peroxidase-labeled goat anti-rat antibody (Jackson Immunoresearch, West Grove Pa.) and ABTS/H$_2$O$_2$ (ELISA) (wherein ABTS is 2, 2'-azino-bis(3-ethylbenzthiazoline-6-sulfonic acid)) or DAB/H$_2$O$_2$ (WESTERN) (wherein DBS is 3,3'-diaminobenzidine). IgG from reactive sera was then extracted on protein A Sepharose and tested for the ability to inhibit HT1080 cell attachment to peak 2. Spleen cells from a rat with adhesion inhibitory antibodies were fused with rat YB2 myeloma cells (43) according, to standard procedures. Hybridoma supernatants were screened for reactivity with peak 2 by ELISA, and then screened for inhibition of HT1080 cell attachment to peak 2 by preincubation of peak 2 coated A, cells with hybridomas grown in 'Protein-Free Medium' (Gibco; Grand Island N.Y.) supplemented with 0.5% serum. Neutralizing antibodies were subsequently screened for inhibition of regulated secretion resulting in the identification of 3E12G11D6D2Y ('3E12'); determined to be IgG2a by the Ouchterlony method. 3E12 was purified from supernatants by ammonium sulfate precipitation followed by goat anti-rat IgG, F(ab')$_2$ affinity chromatography.

Characterization of 3E12 Mab—For competitive ELISA experiments purified 3E12 mab was incubated overnight (4° C.) with increasing amounts (0.001 µM–1µM) of soluble laminin, collagen IV, entactin, fibronectin, vitronectin, BM-40 or perlecan core protein, followed by an overnight incubation (4° C.) of the antibody/competitor mixture with peak 2 immobilized in wells (2 µg/ml) of 96 well plates. Detection was with peroxidase labeled goat anti-rat IgG and ABTS-H$_2$O$_2$. For Western blots, BMS was separated by SDS PAGE on 5–15% gradient gels and transferred in Tris-glycine-methanol to nitrocellulose. Blots were blocked with 5% milk, phosphate buffered saline (PBS), 0.1% Tween and incubated with 3E12 mab. Blots were incubated with a secondary peroxidase-conjugated goat anti-rat F(ab')$_2$ specific antibody (Jackson Immunoresearch, West Grove Pa.) or alternatively a peroxidase-labeled sheep anti-rat antibody (Amersham, Arlington Heights Ill.) which had been preabsorbed on a BMS-Sepharose column to eliminate background. 6 M guanidine HCl extracts of mouse (C57BL/6; NCI, Frederick Md.) lacrimal and parotid glands, kidney, brain, pancreas and lung were prepared according to the method of Hunter et al (44) in the absence of DTT.

Statistical Analysis—All values are expressed as the mean ± the standard error of the mean. Student's t test was used where noted to assess statistical significance.

RESULTS

Figure 1B:
Figures 2, 2A:
FIGS. 2a and 2b. Regulated and constitutive secretary pathways are active in BMS-adherent rat lacrimal acinar cells.
Figures 1, 2A:
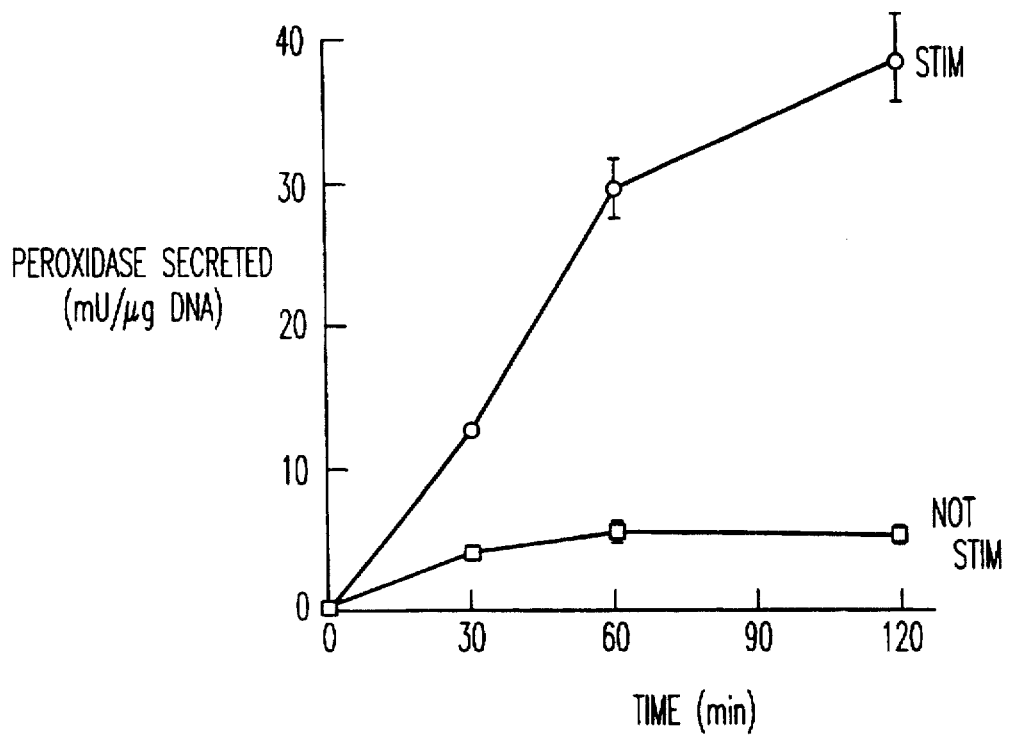
Figure 2B:
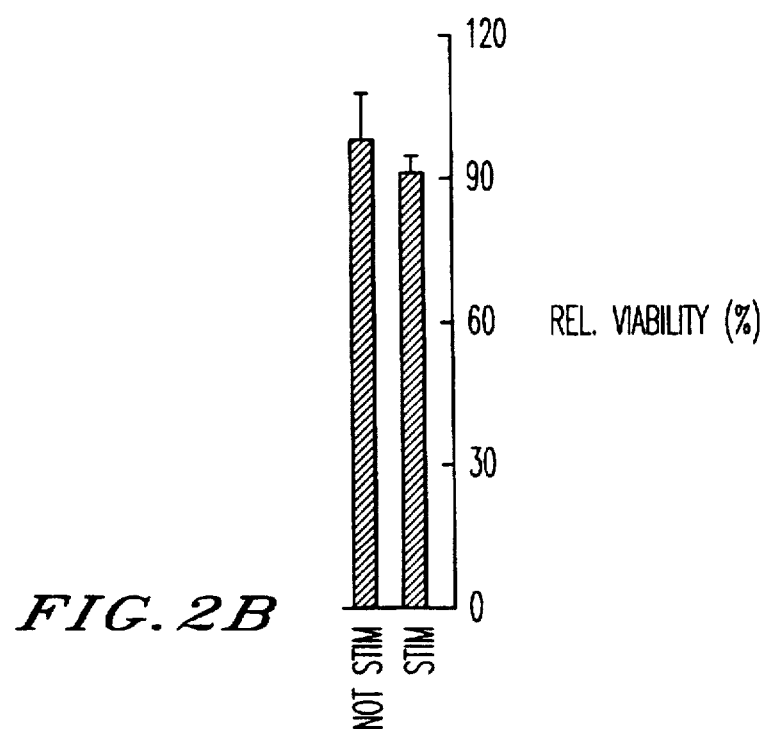
Figure 5A:
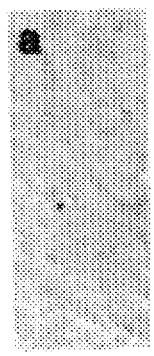
Figure 5B:
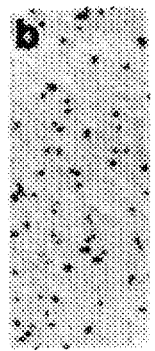
Figure 5C:
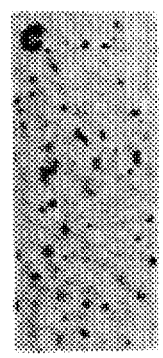
Figure 5D:
Figures 1, 5E:
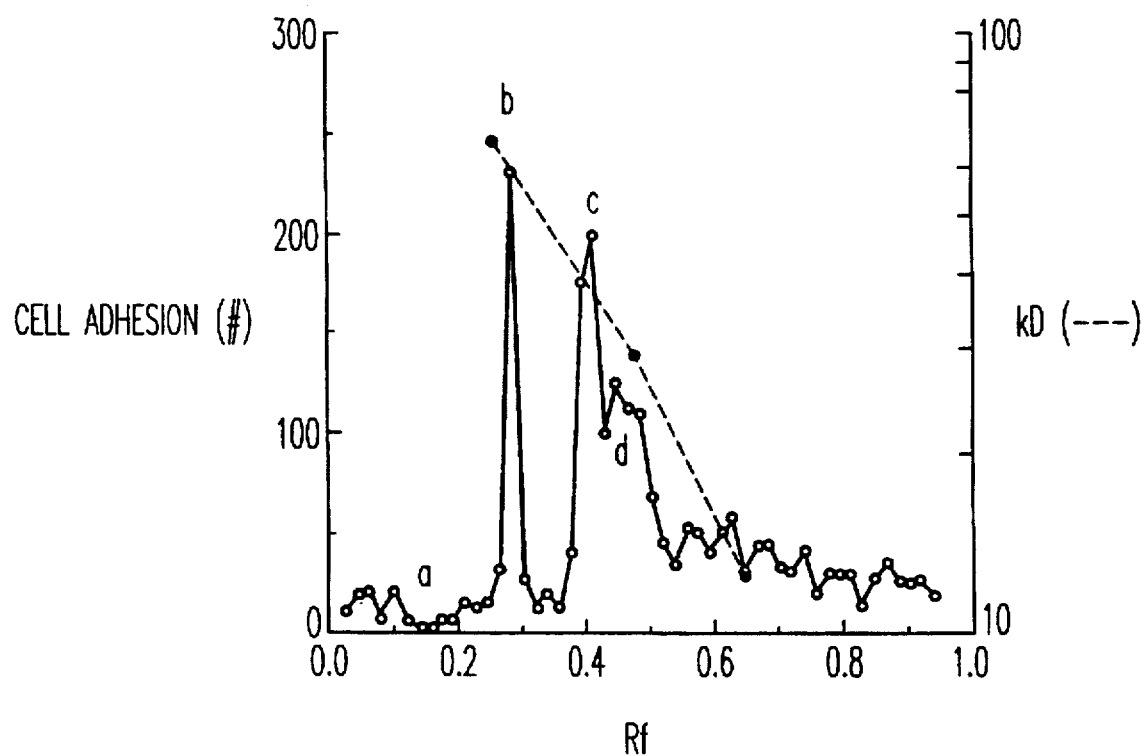

Adhesion to Basement Membrane Supports Regulated Secretion—Basement membrane is a prominent histological feature of the lacrimal gland acinus. Using 'BMS', a 10 mM EDTA extract of mouse EHS basement membrane, and its constituent (FIGS. 1a and 1b) high (peak 1) and low (peak 2) molecular weight peaks we set out to ask whether adhesion to basement membrane is functionally linked to stimulus-secretion coupling. Freshly isolated lacrimal acinar cells adhered to gelled BMS, and after 24 hr (FIGS. 2a and 2b) or 48 hr (not shown) were responsive to carbachol and VIP in a time (FIG. 2a) and dose (not shown) dependent manner without loss of viability (FIG. 2b). In contrast, cells maintained for the same period in suspension or adherent to plastic deteriorated and/or were poorly responsive (not shown).

Identification of BMS associated activity(s) was initiated by plating cells on BMS versus on equal milligram amounts of gelled laminin purified from peak 1 (FIGS. 3a and 3b). BMS adherent cells were twice (FIG. 3b; cumulative regulated secretion over the first 100 min) as responsive to carbachol and VIP as cells attached to laminin. This difference in rate (FIG. 3a) of secretion was not an artifact of cell number since all secretion values were normalized to cellular DNA, and constitutive peroxidase secretion by cells on the two substrates was identical (not shown). Rupture of cell membranes by sonication and freeze-thawing revealed that similar amounts of intracellular peroxidase were available for release (FIG. 3a, inset), and the effect appeared to be entactin independent (not shown).

Figures 2, 5E:
FIGS. 5a–5e. HT1080 cells attach to DTT reduced peak 2 proteins of 60, 35 and 30 Kda, as revealed by blot adhesion assays.

Peak 2 Contains Cell Adhesion Activity—The implication of these studies was that a peak 2 secretion enhancing activity was required to achieve maximal levels of regulated secretion. We presumed that the putative activity may be adhesive to cells and carried out attachment studies (FIGS. 4a and 4b) using freshly isolated lacrimal acinar cells and HT1080 human fibrosarcoma cells, the latter of which had the advantage of known avidity for basement membrane. Coating with increasing amounts of peak 2 resulted in a dose dependent increase in cell adhesion which was maximal at 3–5 µg/well (FIG. 4a); achieving a level Similar to 4 µg/well of peak 1, purified laminin or BMS (FIG. 4a, inset). Lacrimal acinar cells adhered at a lower level (FIG. 4b), as is often observed for primary cultures. To determine the size of peak 2 adhesion activity, cells were incubated with blots of peak 2 previously separated on SDS PAGE gels under reducing conditions (FIGS. 5a–5e). Examination in the light microscope revealed regions of few (FIG. 5a) or many (FIG. 5b–d) dark staining adherent cells which when quantitated relative to Rf (FIG. 5e) pointed to adhesive activities at 60, 35 and 30 kDa[1]. Reexamination of several M$_r$ vs Rf plots establish these values as 60, 35 and 30 kD.; corresponding to proteins of similar size (FIG. 5e, inset).

[1]Approximate molecular weights of adhesion activity was previously reported as 65, 40 and 25 kD in meeting abstracts (Laurie et al, Inv. Opthalmol. Vis. Sci. 33: 1289a, 1992; Laurie et al, Mol. Biol. Cell 3: 75a, 1992)

3E12 Mab Inhibits Peak 2 Adhesion and Secretion Enhancing Activity—Rat monoclonal antibodies were prepared against peak 2 and screened for the ability to block cell adhesion to peak to peak 2; with a subsequent screen for inhibition of peak 2 secretion enhancing activity. Several adhesion neutralizing antibodies were identified (not shown), among which 3E12 mab (FIG. 6a) was also found to inhibit the secretion enhancing activity (FIG. 6b). 3E12 had no effect on cell adhesion to laminin or collagen IV (FIG. 6a). Thus in secretion experiments adhesion to BMS in the presence of 3E12 mab was near normal (aided also by fibronectin and/or vitronectin in the serum). 3E12 mab had no effect on constitutive secretion (not shown), nor total cellular peroxidase (FIG. 6b, inset) and no differences were apparent in cell viability (not shown).

Figures 1, 7B:
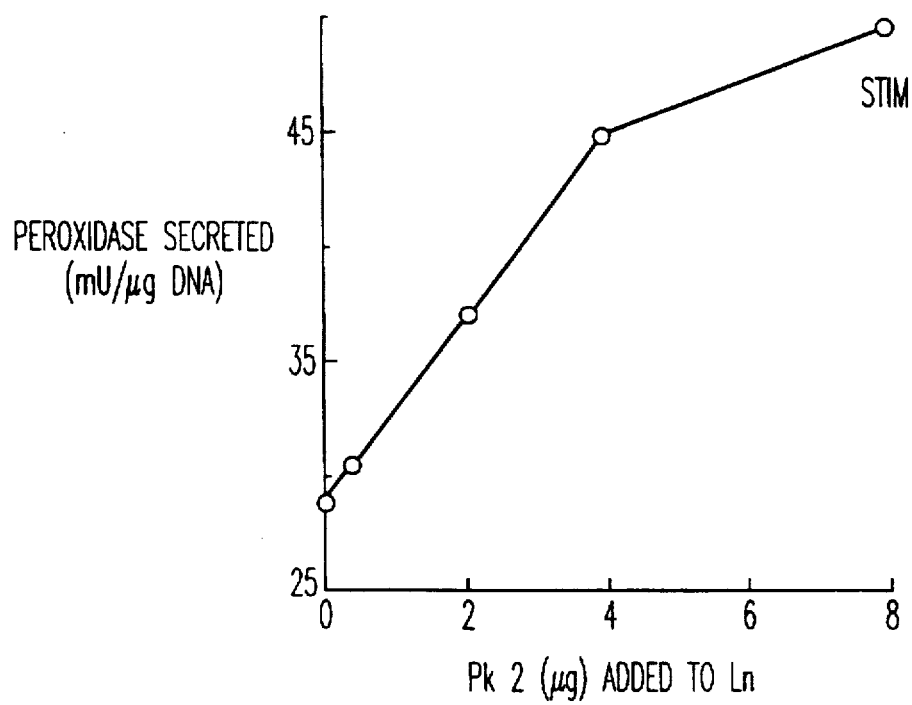
Figures 2, 7B:
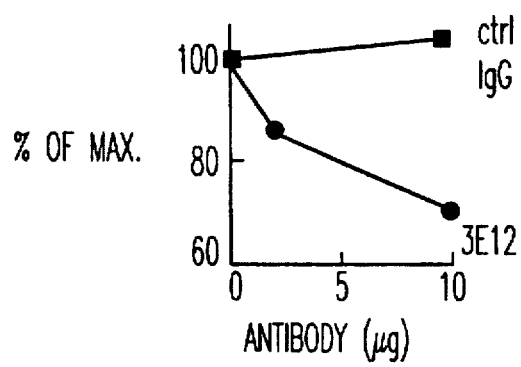

These data were subsequently confirmed by addback experiments using coated substrates in the presence or absence of antibody. Co-coating laminin with increasing microgram amounts of peak 2 under conditions in which both substrates become immobilized on plastic gave rise to (FIGS. 7a and 7b) a peak 2 dose dependent increase in regulated (FIG. 7b) but not constitutive (FIG. 7a) secretion. Cell adhesion was constant and regulated secretion remained at approximately 26–28 mU/µg cellular DNA when peak 2 or laminin were respectively coated alone at increasing amounts. Addition of 3E12 mab to laminin/peak 2 resulted in a dose dependent decrease in regulated secretion (FIG. 7b, inset). No change was observed with a control antibody (FIG. 7b, inset).

Figure 8B:
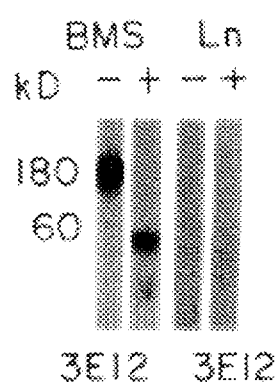
FIG. 8. 3E12 mab recognizes a 180 Kda trimer (designated 'BM180') which does not appear to be immunologically related to other basement membrane proteins. Competitive ELISA illustrating lack of 3E12 mab interaction with entactin (En), vitronectin (Vn), fibronectin (Fn), perlecan core protein (Pn), collagen IV (CIV), BM40 or laminin (Ln) which served as competitive inhibitors. Inset, BMS Western blot illustrating migration of BM180 without (−) and with (+) prior DTT reduction. BM180 is not detected in blots of purified laminin (Ln). Molecular weights were estimated from semi-log $M_r$ vs $R_f$ plots. The wide BM180 band represents a slight overexposure to confirm antibody specificity.
Figure 9:
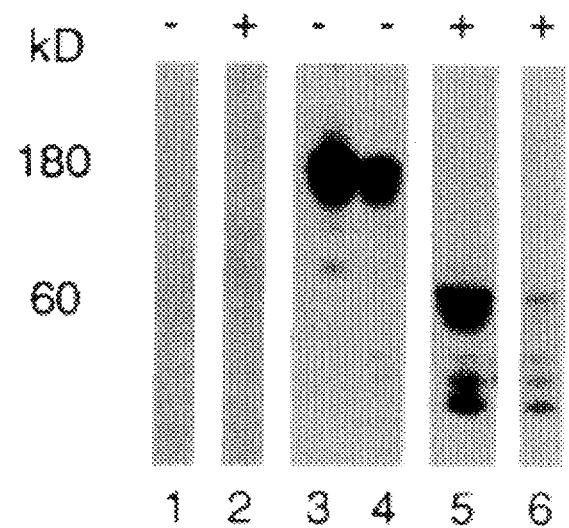
FIG. 9. Presence of BM180 in peak 2. Lanes 1 and 2: negative control BMS blots without (−) and with (+) prior DTT reduction in which secondary antibody alone was applied to blot. Lanes 3 (without DTT;−) and 5 (with DTT;+): 3E12 mab detection of BM180 in peak 2 prepared by solubilization of BMS with 30% ammonium sulfate. Lanes 4 (without DTT;−) and 6 (with DTT; +): detection of BM180 in peak 2 prepared by gel filtration. BM180 is somewhat sensitive to NEM and PMSF inhibitable proteolysis during chromatography or ammonium sulfate solubilization.
Figure 8A:
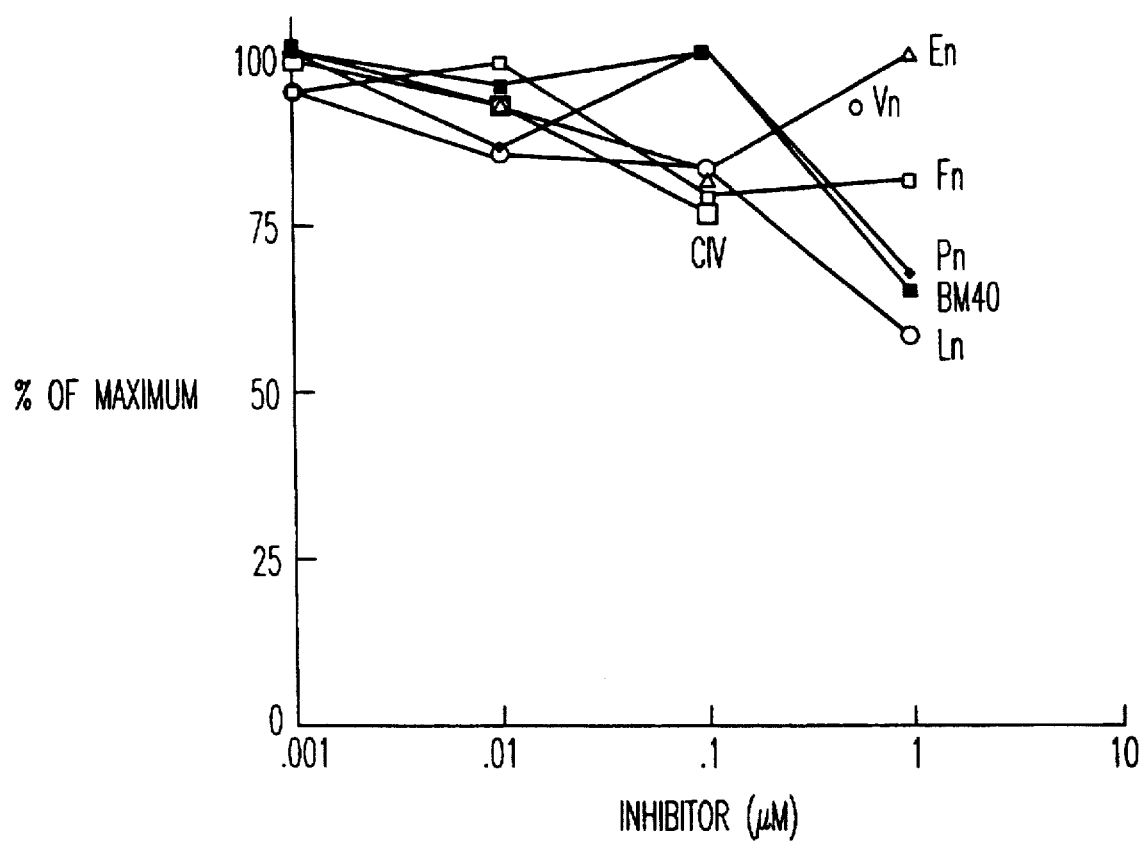

3E12 Antigen 'BM180' is Enriched in Lacrimal and Parotid Glands—Characterization of 3E12 mab by competitive ELISA revealed no apparent immunological reactivity with the isolated matrix macromolecules laminin, collagen IV, entactin, perlecan core protein, BM-40, fibronectin or vitronectin which were individually tested for inhibitory activity in this assay (FIG. 8). On Western blots of BMS (FIG. 8, inset) or peak 2 (FIG. 9, lanes 3–6) 3E12 mab reacted with a 180 kDa protein (designated 'BM180') which migrated at 60 kDa upon reduction. 3E12 mab showed no reactivity with blots of purified laminin (FIG. 8, inset) and BMS blots incubated with secondary antibody alone followed by detection were completely blank (FIG. 9, lanes 1, 2). These results were in agreement with a 60 kDa adhesive activity in blots of reduced peak 2 (FIG. 5). Although 180 kDa proteins were not obvious in Coomassie blue stained SDS PAGE gels of nonreduced peak 2 at usual loading levels, they became apparent upon heavier loading (FIG. 1b).

Figure 10:
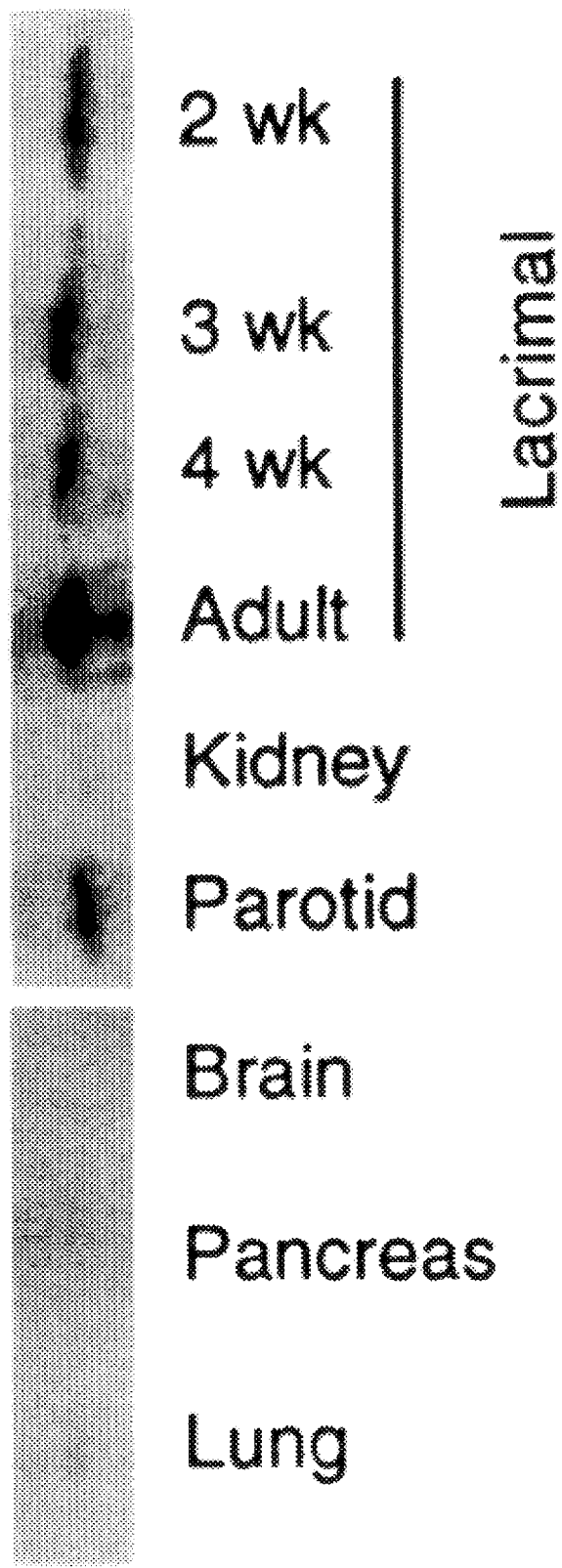
FIG. 10. BM180 is enriched in lacrimal and parotid glands, weak in lung but not apparent in kidney, brain or pancreas. 6 M guanidine Hcl tissue extracts were loaded equally by weight without prior DTT reduction, separated on the same sodium dodecyl sulfate polyacrylamide gel electrophoresis (SDS PAGE) gel and transferred. BM180 detection was with 3E12 mab. Figure is of same blot and exposure time.

Since 3E12 mab has not proven amenable to tissue immunostaining, distribution was examined in Western blots using 6 M guanidine-HCl extracts of mouse adult lacrimal and parotid, glands, kidney, brain, pancreas and lung. We also tested postnatal lacrimal gland at 2 wk (when eyelids first open), 3 and 4 wk. These experiments gave rise to the observation (FIG. 10) that guanidine-Hcl extractable BM180 was enriched in lacrimal and parotid glands, slightly detectable in lung and not apparent in kidney, brain or pancreas.

REFERENCES CITED

1. Watt, F. W. (1991) FASEB J. 5, 287–294.
2. Hay, E. D. (1993) Curr. Opin. Cell Biol. 5, 1029–1035.
3. Lin, C. Q., and Bissell, M. J. (1993) FASEB J. 7, 737–743.
4. White, J. M. (1992) Science 258, 917–924.
5. Jamieson, J. D. et (1988) Scand J. Gastroenterol. Suppl., 151 98–103.
6. Burgess, T. L., and Kelly, R. B. (1987) Annu. Rev. Cell Biol. 3, 243–293.
7. Castle, J. D. 1990) Adv. Cell Biol. 3, 251–275.
8. Golosow, N., and Grobstein, C. (1962) Devel. Biol. 4, 242–255.
9. Jamieson, J. D. (1982) Prog. Clin. Biol. Res. 91, 413–427.
10. Pictet, R. L., et al, (1972) Devel. Biol. 29, 436–467.
11. Chang, A., and Jamieson, J. D. 1986) J. Cell Biol. 103, 2353–2365.
12. Larose, L., and Morisset, Jr. (1977) Gastroenterol. 73, 530–533.
13. Werlin, S. L., and Stefaniak, J. (1982) Pediatr. Res. 16, 123–125.
14. Gumbiner, B., and Kelly, R. G. (1981) Proc. Natl. Acad. Sci. USA 78, 318–322.
15. Morita, S. et al, (1989) Endocrinol. 124, 2052–2056.
16. Greene, L. A., and Tischler, A. S. (1976) Proc. Natl. Acad. Sci. USA 3, 2424–2429.
17. Gotti, C., et al., (1987) Different. 34, 144–155.
18. Logsdon, C. D. et al, (1985) J. Cell Biol. 100, 1200–1208.
19. Brunet-de Carvalho, N. et al, (1989) Different. 40, 106–118.
20. Amsterdam, A., and Jamieson, J. D. (1974) J. Cell Biol. 63, 1057–1073.
21. Herzog, V. et al, (1976) J. Cell Biol. 70, 692–706.
22. Parod, R. J., and Putney, J. W., Jr. (1980) Am. J. Physiol. 236, 6106–6113.
23. Arvan, P., and Castle J. D. (1987) J. Cell Biol. 104, 243–252.
24. Oliver, C. et al, (1987) In Vitro Cellul. & Devel. Biol. 23, 465–473.
25. Arias, A. E., and Bendayan, M. (1991) Exp. Cell Res. 195, 199–206.
26. Dartt, D. A. et al, (1984) Am. J. Physical 247, 6502–6509.
27. Busson-Mabillot, S. et al, (1982) J. Cell Biol. 95, 105–117.
28. Matter, M. L., and Laurie, G. W. (1994) J. Cell Biol 124, 1083–1090.
29. Paulsson, M. et al, (1987) Eur. J. Biochem. 166, 11–19.
30. Markwell, M. A. et al, (1978) Anal. Biochem 87, 206–210.
31. Kleinman, H. K. et al, (1982) Biochem 24, 6188–6193.
32. Laurie, G. W. et al, (1988) Am. J. Anat. 181, 320–326.
33. Hann, L. E., Keller, R. S., and Sullivan, D. A. (1991) Invest. Opthalmol. Vis. Sci. 32, 2610–2621.
34. Yurchenco, P. D. et al, (1985) J. Biol Chem. 260, 7636–7644
35. Laurie, G. W. et al, (1986) J. Mol. Biol. 189, 205–216.
36. Kleinman, H. K. et al, (1986) Biochem. 25, 312–318.
37. Labarca, C., and Paigen, K. (1980) Anal. Biochem., 102, 344–354.
38. Aumailley, M. et al, (1989) Exp. Cell Res. 181, 463–474.
39. Aumailley, M. et al, (1987) J. Biol Chem. 262, 11532–11538.
40. Heyman, E. G. et al, (1982) J. Cell Biol 95, 20–23.
41. Engvall, E., and Perlman, P. (1972) J. Immunol. 109, 129–135.
42. Towbin, H., et al, (1979) J. Immunol. 116, 676–681.
43. Kilmartin, J. V. et al, (1982) J. Cell Biol. 93, 576–582.
44. Hunter, D. D. et al, (1992) Neuron 8, 399–413.
45. Paulsson, M., and Heinegard, D. (1981) Biochem. J. 197, 367–375.
46. Bao, Z. Z. et al, (1992) J. Biol. Chem. 267, 4974–4980.
47. Blum, J. L. et al, (1987) Exp. Cell Res. 173, 322–340.
48. Li, M. L. et al, (1987) Proc. Natl. Acad. Sci. USA. 84, 136–140.
49. Rodriguez-Boulan, E., and Nelson, W. J. (1989) Science 245, 718–725.
50. Bissell, M. J., and Barcellos-Hoff, M. H. (1987) J. Cell Sci. Suppl. 8, 327–343.
51. Gardner, J. D., and Jensen, R. T. (1981) in Physiology of the Gastrointestinal Tract (Johnson, L. R., ed) pp. 831–871, Raven Press, New York.
52. Adams, J. C., and Watt, F. W. (1993) Development 117, 1183–1198.

Having now fully described the invention, it will be apparent to one of ordinary skill in the art that many changes and modifications can be made thereto without departing from the spirit or scope of the invention as set forth herein.

What is claimed as new and is desired to be secured by Letters Patent of the United States is:

1. A monoclonal antibody, wherein said monoclonal antibody is 3E12 expressed by the hybridomal cell line as deposited with the American Type Culture Collection under accession number HB-11879.

* * * * *